United States Patent
Shirley et al.

(10) Patent No.: US 9,204,630 B2
(45) Date of Patent: Dec. 8, 2015

(54) CAPSULE FORMULATION

(75) Inventors: Ian Malcolm Shirley, Bracknell (GB); Tanya Wright, Basel (CH); Robert Michael Perrin, Bracknell (GB); Patrick Mulqueen, Bracknell (GB); Anne Waller, Bracknell (GB); Andy Pierce, Bracknell (GB)

(73) Assignee: Syngenta Participations AG, Basel (CH)

( * ) Notice: Subject to any disclaimer, the term of this patent is extended or adjusted under 35 U.S.C. 154(b) by 1634 days.

(21) Appl. No.: 11/817,068

(22) PCT Filed: Feb. 23, 2006

(86) PCT No.: PCT/EP2006/001657
§ 371 (c)(1),
(2), (4) Date: Aug. 19, 2008

(87) PCT Pub. No.: WO2006/089747
PCT Pub. Date: Aug. 31, 2006

(65) Prior Publication Data
US 2008/0306026 A1    Dec. 11, 2008

(30) Foreign Application Priority Data

Feb. 24, 2005    (EP) .................................... 05004006

(51) Int. Cl.
| | | |
|---|---|---|
| *A01N 25/00* | (2006.01) | |
| *A01N 47/34* | (2006.01) | |
| *A01N 53/00* | (2006.01) | |
| *A01N 47/12* | (2006.01) | |
| *A01N 47/40* | (2006.01) | |
| *A01N 25/22* | (2006.01) | |
| *A01N 25/28* | (2006.01) | |
| *A01N 43/90* | (2006.01) | |
| *A01N 47/02* | (2006.01) | |

(52) U.S. Cl.
CPC ................ *A01N 25/22* (2013.01); *A01N 25/28* (2013.01); *A01N 43/90* (2013.01); *A01N 47/02* (2013.01)

(58) Field of Classification Search
CPC ... A01N 2300/00; A01N 43/90; A01N 47/02; A01N 25/22; A01N 25/28
See application file for complete search history.

(56) References Cited

U.S. PATENT DOCUMENTS

| | | | | |
|---|---|---|---|---|
| 4,440,756 | A * | 4/1984 | Herve et al. .................... | 514/521 |
| 6,395,776 | B1 * | 5/2002 | Losel et al. .................... | 514/531 |
| 2002/0037306 | A1 * | 3/2002 | Van Koppenhagen et al. ............................. | 424/408 |
| 2004/0198704 | A1 * | 10/2004 | Shuster et al. ................ | 514/151 |
| 2004/0235898 | A1 * | 11/2004 | Klein et al. .................... | 514/318 |

FOREIGN PATENT DOCUMENTS

| | | |
|---|---|---|
| CN | 1386419 A | 12/2002 |
| CN | 1491552 A | 4/2004 |
| DE | 4009141 A1 | 9/1990 |
| DE | 19503157 A1 | 8/1995 |
| EP | 0761096 A | 3/1997 |
| WO | 89/04170 A | 5/1989 |
| WO | 00/05951 A | 2/2000 |

OTHER PUBLICATIONS

Anonymous, "Pyrethrinoids Stabilized by Non—azo—dyes", Research Disclosure No. 22221, Oct. 1982, XP002408404, whole document.

* cited by examiner

*Primary Examiner* — Kyle Purdy
(74) *Attorney, Agent, or Firm* — Brian D. McAlhaney

(57) ABSTRACT

An encapsulated composition of (a) a pesticide at least active via ingestion that is photolabile, and (b) at least one photoprotectant, wherein the encapsulating polymeric barrier is base triggerable is disclosed. A method for controlling damage of a material by a pest by the use of such encapsulated compositions is likewise disclosed. The composition as disclosed gives protection for beneficial arthropods and reduces workers exposure.

17 Claims, 1 Drawing Sheet

Figure 1 - Photostability of emamectin benzoate coencapsulated with photoprotectants

PHOTOSTABILITY OF EMAMECTIN BENZOATE COENCAPSULATED WITH PHOTOPROTECTANTS

AFTER 5 HRS IRRADIATION
AFTER 24 HRS IRRADIATION

| Example | After 5 hrs | After 24 hrs |
|---|---|---|
| EXAMPLE 3 | 2 | 0 |
| EXAMPLE 7 | 68 | 6 |
| EXAMPLE 9 | 8 | 0 |
| EXAMPLE 8 | 22 | 1 |
| EXAMPLE 6 | 39 | 1 |
| EXAMPLE 11 | 78 | 20 |
| EXAMPLE 10 | 76 | 18 |

Figure 2 - Photostability of emamectin benzoate coencapsulated with photoprotectants

PHOTOSTABILITY OF EMAMECTIN BENZOATE COENCAPSULATED WITH PHOTOPROTECTANTS

AFTER 5 HRS IRRADIATION
AFTER 24 HRS IRRADIATION

| Example | After 5 hrs | After 24 hrs |
|---|---|---|
| EXAMPLE 3 | 2 | 0 |
| EXAMPLE 21 | 64 | 10 |
| EXAMPLE 19 | 34 | 1 |
| EXAMPLE 20 | 55 | 4 |
| EXAMPLE 22 | 57 | 14 |
| EXAMPLE 24 | 49 | 13 |
| EXAMPLE 23 | 54 | 14 |

CAPSULE FORMULATION

This application is a 371 of International Application No. PCT/EP2006/001657 filed Feb. 23, 2006, which claims priority to EP 05004006.2 filed Feb. 24, 2005, the contents of which are incorporated herein by reference.

The present invention relates to a method for improving the delivery of a pesticide to its target site, where the pesticide is at least active via ingestion and is photolabile, and encapsulated compositions for such a method.

There is a need for effective ways of controlling the damage of materials, such as plants and construction materials, by pests. Many such pests have alkaline conditions in the gut. Additionally many pesticides including insecticides active via ingestion are photolabile and suffer loss of efficacy in sunlight. Furthermore, it is desirable to improve selectivity of said insecticides to beneficial insects and minimize operator exposure during use.

Capsule technologies have been in existence for a number of years (see, for example, GB1513614, CA2133779, WO00/05951, U.S. Pat. No. 6,485,736, and U.S. Pat. No. 5,846,554). By capsule we mean a composition in which one substance is embedded in another substance. Microcapsules for use in the present invention may vary from 0.5 to 1000 micrometers, preferably from 0.5 to 100 micrometers, and particularly preferably from 1 to 40 micrometers.

Base-triggerable capsule technology has also been disclosed for pesticides (see, for example, WO00/05951).

Further, the use of a photoprotectant in capsules to inhibit the photodegradation of an insecticide has been disclosed in WO96/33611, where the capsule contained particulate suspensions selected from titanium dioxide, zinc oxide and mixtures thereof.

By photoprotectant, we mean a compound or combination of compounds that reduce the chemical degradation of a pesticide that is induced by light, typically between the wavelengths of 200 nm to 800 nm. Such degradation is typically termed photoinstability or photodegradation and said pesticide is deemed to be photolabile, photounstable or photosensitive.

It has now been found that certain compositions containing a pesticide that is both at least active via ingestion and photolabile provide unexpected control of pests that have alkaline conditions in the gut.

The term "ingestion" is understood to refer to the consumption by a pest of an agronomic or non-agronomic material (e.g. plant, bait, foodstuff or other phagostimulatory material) treated with a pesticide. Then the uptake of the said pesticide into said pest principally occurs via the gut.

Accordingly, in a first aspect, the present invention provides a method for controlling damage of a material by a pest, which comprises applying to the material a composition comprising a capsule, which comprises:

(a) a pesticide at least active via ingestion and that is photolabile, and
(b) at least one photoprotectant compound selected from all-trans-(all-E)-1,1'-(3,7,12,16-tetramethyl-1,3,5,7,9,11,13,15,17-octadecanonaene-1,18-diyl)bis[2,6,6-trimethylcyclohexene; 2-ethylhexyl-p-methoxycinnamate; 1,3-bis-[2'-cyano-3',3-diphenylacryloyl)oxy]-2,2-bis-{[2-cyano-3',3'-diphenylacryloyl)oxy]methyl}propane; ethyl 2-cyano-3,3-diphenyl-2-propenoate; 2-ethylhexyl-2-cyano-3,3-diphenylacrylate; 2,3-dihydro-1,3,3-trimethyl-2-[(2-methyl-3H-indol-3-ylidene)ethylidene]-1H-Indole, monohydrochloride; 3,6-diamino-10-methylacridinium chloride+3,6-diaminoacridine; monosodium 1-amino-9,10-dihydro-9,10-dioxo-4-(phenylamino)-2-anthracenesulfonate; 1-amino-2-methyl-9,10-anthracenedione; 1,4-bis[(1-methylethyl)amino]-9,10-anthracenedione; 1,4-bis[(4-methylphenyl)amino]-9,10-anthracenedione; 1-hydroxy-4-[(4-methylphenyl)amino]-9,10-anthracenedione; monosodium 4-hydroxy-3-[(2-hydroxy-1-naphthalenyl)azo]-benzenesulfonate; monosodium 4-[(2-hydroxy-1-naphthalenyl)azo]-3-methyl-benzenesulfonate; 4-[(4-nitrophenyl)azo]-N-phenyl-benzenamine; 4-[[4-(phenylazo)-1-naphthalenyl]azo]-phenol; 3-[ethyl[4-[(4-nitrophenyl)azo]phenyl]amino]-propanenitrile; 4-[(4-nitrophenyl)azo]-benzenamine; monosodium 3-hydroxy-4-[(1-hydroxy-2-naphthalenyl)azo]-7-nitro-1-naphthalenesulfonate; 1-[[2,5-dimethyl-4-[(2-methylphenol)azo]phenyl]azo]-2-naphthalenol; 1-[[4-[(dimethylphenyl)azo]dimethylphenyl]azo]-2-naphthalenol; 1-(ortho-tolylazo)-2-naphthol; tetrasodium 4-amino-5-hydroxy-3,6-bis[[4-[[2-(sulfooxy)ethyl]sulfonyl]phenyl]azo]-2,7-naphthalenedisulfonate; 1-[[4-(phenyl)azo)phenyl]azo]-2-naphthalenol; 1-[[3-methyl-4-[(3-methylphenol)azo]phenyl]azo]-2-naphthalenol; 2,3-dihydro-2,2-dimethyl-6-[[4-(phenylazo)-1-naphthalenyl]azo]-1H-perimidine; 1-(phenylazo)-2-naphthalenol; 1-[[2-methyl-4-[(2-methylphenol)azo]phenyl]azo]-2-naphthalenol; 1,3(2H)-dione, 2-(3-hydroxy-2-quinolinyl)-1H-indene; 2-(1,3-dihydro-3-oxo-2H-indol-2-ylidene)-1,2-dihydro-3H-indole-3-one; disodium 2-(1,3-dihydro-3-oxo-5-sulfo-2H-indol-2-ylidene)-2,3-dihydro-3-oxo-1H-indole-5-sulfonate; mixture of 1-(phenylazo)-2-naphthalenol with 1,4-bis[(1-methylethyl)amino]-9,10-anthracenedione; mixture of 1-(phenylazo)-2-naphthalenol with 1,4-bis[(1-methylethyl)amino]-9,10-anthracenedione and 1-[[2-methyl-4-[(2-methylphenol)azo]phenyl]azo]-2-naphthalenol; benzo[a]phenoxazin-7-ium, 5-amino-9-(diethylamino)-, sulfate; N-[4-[[-(diethylamino)phenyl](2,4-disulfophenyl)methylene]-2,5-cyclohexadien-1-ylidene]-N-ethyl-ethanaminium, inner salt, sodium salt; N-[4-[[4-(dimethylamino)phenyl][4-(phenylamino)-1-napthalenyl]methylene]-2,5-cyclohexadien-1-ylidene]-N-methyl-methanaminium chloride; N-[4-[[4-(dimethylamino)phenyl][4-(ethylamino)-1-napthalenyl]methylene]-2,5-cyclohexadien-1-ylidene]-N-methyl-methanaminium chloride; 4,5,6,7-tetrachloro-3',6'-dihydroxy-2',4',5',7'-tetraiodospiro[isobenzofuran-1(3H), 9'-[9H]xanthen]-3-one disodium salt; 2-(3,4-dihydroxyphenyl)-3,5,7-trihydroxy-4H-1-benzopyran-4-one; N,N',N'',N'''-tetrakis(4,6-bis(butyl-(N-methyl-2,2,6,6-tetramethylpiperidin-4-yl)amino)triazin-2-yl)-4,7-diazadecane-1,10-diamine; poly[[6-[(1,1,3,3-tetramethylbutyl)amino]-1,3,5-triazine-2-4-diyl][2,2,6,6-tetramethyl-4-piperidinyl)imino]-1,6-hexanediyl[(2,2,6,6-etramethyl-4-piperidinyl)imino]]); mixture of esters of 2,2,6,6-tetra-methyl-4-piperidinol with higher fatty acids (mainly stearic and palmitic acids); propanedioic acid, [(4-methoxyphenyl)-methylene]-, bis(1,2,2,6,6-pentamethyl-4-piperidinyl)ester; bis(2,2,6,6-tetramethyl-4-piperidyl) sebaceate; bis (1,2,2,6,6-pentamethyl-4-piperidinyl)ester; polymer of N,N'-bis(2,2,6,6-tetramethyl-4-piperidinyl)-1,6-hexanediamine with 2,4,6-trichloro-1,3,5-triazine reaction products with 3-bromo-1-propene, N-butyl-1-butanamine and N-butyl-2,2,6,6-tetramethyl-4-piperidinamine, oxidised, hydrogenated; 4-methyl-2,6-di-tert-butylphenol; octadecyl-3,5-di-tert-butyl-4-hydroxyhydrocinnamate; 2-tert-butyl-1,4-benzenediol; '2,2'-dihydroxy-4-methoxybenzophenone; 2-hydroxy-4-methoxybenzophenone; 2-hydroxy-4-n-octyloxybenzophenone; 2-(4-diethylamino-2-hydroxybenzoyl)-benzoic acid, hexyl ester; 2,2',4,4'-tetrahydroxybenzophenone;

'2(2'-hydroxy-5'-t-octylphenyl)benzotriazole; α-[3-[3-(2H-benzotriazol-2-yl)-5-(1,1-dimethylethyl)-4-hydroxyphenyl]-1-oxopropyl]-ω-hydroxy-poly(oxy-1,2-ethanediyl); 2-(2'-hydroxy-3'-dodecanyl-5'-methylphenyl)-benzotriazole; 2-(2H-benzotriazol-2-yl)-4,6-bis(1-methyl-1 phenylethyl)phenol; '2-(2'-hydroxy-3'-t-butyl-5'-methylphenyl)-5-chlorobenzotriazole; '2-(2'-hydroxy-3,5-di-t-butylphenyl)-5-chlorobenzotriazole; 2-(2H-benzotriazol-2-yl)-4,6-di-tert-pentylphenol; 3-(2H-benzotriazol-2-yl)-5-(1,1-dimethylethyl)-4-hydroxy-benzenepropanoic acid, C7-9 branched and linear alkyl esters; 2-[4,6-bis(2,4-dimethylphenyl)-1,3,5-triazin-2-yl]-5-[2-hydroxy-3-(dodecyloxy- and tridecyloxy)propoxy]phenols; zinc oxide; titanium dioxide; mixture of zinc oxide and titanium dioxide; micronised carbon black; 3,5,6-trihydroxybenzoic acid n-propyl ester; sodium iodide; 2,2'-thiobis[4-t-octylphenolato]-beta-butylamine nickel (II); 2-ethyl,2'-ethoxyoxalanilide; 3,9-bis(octadecyloxy)-2,4,8,10-tetraoxa-3,9-diphosphaspiro[5.5]undecane+1,1',1"-nitrilotris-2-propanol; 3,9-bis[2,4-bis(1-methyl, 1-phenylethyl)phenoxy]-2,4,8,10-tetraoxa, 3,9-diphosphaspiro[5.5]undecane; tris(2,4-di-tert-butylphenyl) phosphite; 1,2-dihydroxyanthraquinone; 7-β-D-glucopyranosyl-9,10-dihydro-3,5,6,8-tetrahydroxy-1-methyl-9,10-dioxo-2-anthracenecarboxylic acid; 5-hydroxy-1,4-naphthoquinone; sodium sulfite; distearyl-disulfide; distearylthiodipropionate;

and each thereof optionally in combination with a butylated hydroxy anisole; and wherein the polymeric barrier or moieties within the polymeric barrier of the capsule are base cleavable.

In a second aspect, the present invention provides a composition as defined in the first aspect.

In a third aspect, the present invention provides a capsule as defined in the first aspect.

In an embodiment of each aspect of the invention the capsule consists essentially, preferably consists, of (a)+(b) as defined in the first aspect.

The capsules according to the present invention are characterised by the encapsulation of the pesticide and at least one photoprotectant within a base cleavable polymeric barrier; they are designed so as to break down or disintegrate relatively quickly under basic conditions so as to release the encapsulated pesticide into the surrounding environment.

DESCRIPTION OF THE FIGURES

FIG. 1: Photostability of emamectin benzoate coencapsulated with different photoprotectants.

FIG. 2: Photostability of emamectin benzoate coencapsulated with different photoprotectants.

The invention is described in detail below.

In the instance the capsule is not in a basic environment, it functions as a diffusion controlled release formulation. A particular advantage of the present invention is that the release via diffusion is minimised, whilst still allowing rapid release under basic conditions, so as to give minimal activity upon contact whilst maintaining high activity upon ingestion.

The encapsulating polymeric barrier may contain any base-sensitive moieties such that the polymeric barrier is "triggered" or breakdown is initiated when subjected to basic conditions, preferably in a situation in which the resulting pH is from about 8 to about 13, more preferably from about 8 to about 11.

In one preferred embodiment the encapsulating polymeric barrier is of the aminoplast chemistry, produced by a microencapsulation process comprising reacting an amino resin prepolymer with a compound having one or more ester or thioester groups which are cleavable under basic conditions and two or more other functional groups capable of reacting with the resin. Preferably the amino resin is an etherified resin.

Preferably the ester or thioester containing compound is a cross-linking agent produced by reaction of a multifunctional $C_1$-$C_{20}$ aliphatic or cycloaliphatic alcohol containing at least two, preferably at least 3, functional groups which are capable of esterification, such as pentaerythritol, dipentaerythritol, tripentaerythritol, trimethylolpropane, glycerol, mercaptoethanol, 3-mercaptopropane-diol, 1,2,4-butanetriol, 1,3,5-cyclohexanetriol, 1,2,3-heptanetriol, sorbitol, or 2,3-dimercapto-1-propanol with one or more 2-(hydroxy or thiol) substituted $C_2$-$C_6$ alkanoic acids. The processes for producing such compounds and their incorporation into aminoplast capsules are described in WO 0005951 which is incorporated herein by reference.

Preferred base sensitive cross-linkers are made by reacting pentaerythritol with a mixture of glycolic and mercaptoacetic acids.

The process for producing aminoplast or urea-formaldehyde capsules is described in U.S. Pat. Nos. 4,956,129 and 5,160,529 which are incorporated herein by reference, and is generally as follows:

An organic solution or oil phase is provided which comprises the material to be encapsulated, an etherified amino resin prepolymer, preferably dissolved in the material to be encapsulated, and in which from about 50% to about 98% of the methylol groups of the prepolymer have been etherified with a $C_4$-$C_{10}$ alcohol, and the cross-linking agent, the latter preferably dissolved in the material to be encapsulated. Suitable solvents having low solubility in water may be included in the organic phase when the materials to be encapsulated are solids. Then, an emulsion of this organic solution or oil phase is created in a continuous phase aqueous solution comprising water and a surface-active agent, in which the emulsion comprises discrete droplets of the organic phase dispersed in the aqueous phase, such that there is formed an interface between the discrete droplets of the organic phase and the surrounding continuous phase aqueous material. Then, in situ condensation between the resin and cross-linker, and curing of the resulting polymer in the organic phase adjacent to the interface between the phases is produced by simultaneously heating the emulsion to a temperature of from about 20° C. to about 100° C. and adding to the emulsion an acidifying agent, and optionally a phase transfer catalyst, and maintaining the emulsion at a pH of between about 0 and about 4 and a temperature of from about 20 to about 60° C. for a sufficient period of time to allow substantial completion of in situ condensation of the resin prepolymer and cross-linker so as to convert the liquid droplets of the organic phase to capsules which consist of solid permeable polymer polymeric barrier enclosing the encapsulated liquid material.

Preferred solvents for the present invention include alkyl naphthalenes such as those sold under the trade name of Solvesso, and octylmethoxycinnamate.

In another embodiment the encapsulating polymeric barrier is comprised of one or more polythiol compounds, wherein two moles of thiol are coupled together to form a disulfide link which is capable of cleaving under basic conditions. In one particular aspect of this invention these compounds are incorporated into a capsule wall, wherein the wall materials may include an aminoplast resin. Further, with respect to the disulfide links, those links may be already present or pre-prepared in the starting materials used to form the wall, or the links may be generated during wall formation.

The process for producing capsules containing disulfide links is described in U.S. Pat. No. 6,485,736 which is incorporated herein by reference.

In a further embodiment the encapsulating polymeric barrier contains a base-sensitive polymer, examples of which include, inter alia, poly(styrene-co-maleic anhydride), poly (maleic anhydride-alt-1-octadecene) and poly(maleic anhydride-alt-1-tetradecene). These polymers may be incorporated into the encapsulating polymeric barrier via a number of methodologies known to those skilled in the art, including, for example coacervation or solvent evaporation.

The foregoing are descriptions of the production of capsules whereby the encapsulates are suspended in a liquid medium. Alternatively, the suspension may be converted into a dry product by spray drying or other known techniques.

In the embodiment where the encapsulating polymeric barrier is of the aminoplast chemistry with one or more ester or thioester groups which are cleavable under basic conditions, the balance between controlled release via diffusion and rapid release brought about by "triggering" or breakdown when subjected to basic conditions can be controlled by the judicious selection of cross-linking agents that may be used in combination with the compounds that are cleavable under basic conditions. Pentaerythritol derivatives such as pentaerythritol tetrakis (mercaptopropionate) (sold under the trademark Mercaptate Q-43 Ester) are known to be useful as wall modifying agents for urea-formaldehyde capsules, as disclosed, for instance, in U.S. Pat. Nos. 4,956,129, 5,160,529 and 5,332,584. By reacting with ether or methylol groups in the prepolymer, these derivatives increase the degree of cross-linking, strengthening the wall at this time and decreasing its permeability. The base-sensitive cross-linking agents have relatively weak links in the ester and/or thioester groups (—XCO—; where X=O or S) which are alpha to electron-withdrawing oxygen or sulfur atoms which cause the weak links to be susceptible to hydrolysis in the presence of base.

In the aspect in which release via diffusion is minimised, in order to protect beneficial insects for example, the ratio of wall-tightening: base-sensitive cross-linker is chosen so as to minimise diffusion whilst still maintaining rapid release when subjected to basic conditions. The ratio of the wall-tightening: base-sensitive cross-linker may be between about 50:1 and 1:10, preferably between 20:1 and 1:3, even more preferably between 10:1 and 1:1. The total concentration of the cross-linkers may be between about 0.4 and 7.5, preferably between 1 and 4 weight percent of the organic phase.

Preferred wall-tightening cross-linkers used in combination with the base sensitive cross linkers are pentaerythritol tetrakis (mercaptopropionate) and pentaerythritol tetrakis (mercaptoacetate).

The amount of amino resin prepolymer in the organic phase is not critical to the practice of this invention. It is most convenient, however, to use an organic phase of a prepolymer concentration of from about 1% to about 70% on a weight basis, preferably from about 4% to about 50%, particularly preferably from about 5% to about 20%.

The prepolymers useful in the present invention are those known from U.S. Pat. Nos. 4,956,129 and 5,160,529; namely, partially etherified amino resin prepolymers with a high solubility in the organic phase and a low solubility in water. In the non-etherified form, the prepolymer contains a large number of methylol groups in its molecular structure. Etherified prepolymers have the hydroxyl hydrogen atoms replaced by alkyl groups and are obtained by condensation of a compound containing amino groups with formaldehyde and an alcohol. The prepolymers are soluble in the organic phase when the alkyl groups have four or more carbon atoms and in which more than about 50% of the hydroxyl hydrogen atoms on the prepolymer molecule have been replaced. Those useful in the above process are those in which from about 50% to about 98% of the hydroxyl hydrogen atoms have been replaced by alkyl groups, as some hydroxyl groups are needed for the condensation/polymerization which occurs in the wall forming step. Preferably from about 70% to about 90% of the methylol groups have been etherified with preferably a $C_4$-$C_6$ alcohol. The alcohol may be straight or branched chain.

The amino resin may be one of four general types: urea-formaldehyde, melamine-formaldehyde, benzoguanamine-formaldehyde and glycoluril-formaldehyde. The first two mentioned are preferred, with urea-formaldehyde prepolymers being most preferred. The prepolymers utilized may be commercially available etherified amino resin prepolymers. Some commercially available etherified prepolymers are those sold by Cytec under the trademarks Beetle® and Cymel®, the Beckamine® line sold by Reichhold Chemicals, and the Resimen® line sold by Solutia.

Particularly preferred prepolymers are Beetle-80 and Beetle-105010.

The above examples served to illustrate the scope of the invention. It would be obvious to those practised in the art that any amino-formaldehyde condensate that satisfies the criteria of oil solubility and interfacial polymerisation would be suitable.

The prepolymers can also be prepared by known techniques, for instance, by the reaction between the amine (preferably urea or melamine), formaldehyde and alcohol.

Once the organic phase has been formed, an emulsion is then prepared by dispersing the organic phase in an aqueous solution comprising water and a surface-active agent. The relative quantities of organic and aqueous phases are not critical to the practice of this invention, and can vary over a wide range, determined most by convenience and ease of handling. In practical usage, the organic phase will comprise a maximum of about 55% by volume of the total emulsion and will comprise discrete droplets of organic phase dispersed in the aqueous solution.

The surface active agent can be any of the wide variety of compounds known to be useful for lowering the surface tension of a fluid interface, including both nonionic and ionic surface active agents. The quantity of surface active agent is not critical but for convenience generally comprises from about 0.1% to about 10% by weight of the aqueous phase.

Preferred surface active agents include low Mw polyvinylalcohols, copolymers of ethylene oxide and propylene oxide, and sulphonated alkylnaphthalenes.

In some systems emulsion stability can be enhanced by adding a protective colloid to the aqueous phase. The protective colloid stabilizes a dispersed system against aggregation, flocculation and coalescence. Many materials are known to function as protective colloids and are available commercially. The colloid may be added to the aqueous phase prior to the formation of the emulsion or after the emulsion has been formed. The exact quantity of the colloid is not critical; most conveniently between about 0.1% and about 5.0% colloid by weight in terms of the aqueous phase is utilized.

Preferred colloid stabilisers are polyvinylalcohol, sulphonated naphthalene-formaldehyde condensates such as Lomar D supplied by Cognis and sulphonated kraft lignins such as Reax 85A and 100M supplied by Westvaco.

The droplet size of the emulsion is also not critical to the invention. For greatest utility, the droplet size will be in the range of from about 0.5 to about 4,000 microns in diameter, preferably from about 1 micron to about 100 microns in diameter, most preferably from about 1 to about 25 microns in diameter. The emulsion is prepared as is usual, employing any conventional high shear stirrer. Once the desired droplet size is obtained, mild agitation is generally sufficient to prevent proper growth throughout the balance of the process.

Once the desired droplet size has been attained, the overall system is then acidified to a pH of between about 0 and about 4.0, preferably between about 1.0 and about 3.0. This causes the prepolymer and cross-linker to polymerize by condensation in situ and form a polymeric barrier completely enclosing each droplet. Acidification can be accomplished by any suitable means including any water-soluble acid such as formic, citric, hydrochloric, sulfuric, or phosphoric acid, and the like. Acidification can also be achieved by the use of acidic dispersants or surface-active agents that may function as phase transfer catalysts, provided that they are added to the system after the emulsion has been formed.

Sulphonated alkylnaphthalenes are such preferred phase transfer agents that promote interfacial polymerisation.

As the polymer wall becomes more rigid, contact between the active groups on the prepolymer becomes more difficult. Thus, the in situ condensation polymerization reaction is self terminating and is generally allowed to run to completion. However, if desired, the reaction can be arrested before completion by raising the pH. In this manner, the wall tightness, rigidity and permeability can be controlled.

The rate of the in-situ condensation polymerization increases with both acidity and temperature depending on the pH. The reaction can therefore be conducted anywhere within the range or from about 20° C. to about 100° C., preferably between 40° C. and about 60° C. The reaction will generally be complete within a few hours, although with high acidity and high temperature it can be completed within minutes.

The capsules may be post-formulated with anti-settling agents, which include water-soluble polysaccharides such as xanthan gum, water-insoluble polysaccharides such as microcrystalline cellulose and structured clays such as bentonites. Microcrystalline cellulose is a preferred anti-settling agent.

The capsules according to the instant invention are prepared in a manner to obtain either a reservoir capsule or a matrix capsule. Said capsules are preferably reservoir capsules which contain a carrier liquid that is substantially water-immiscible.

The capsules according to the invention are preferably dispersed in the composition, which is advantageously an aqueous medium.

In an embodiment, the capsules are dispersed in an aqueous continuous phase, whilst the carrier liquid inside the capsules is substantially water-immiscible. As used herein, substantially water-immiscible means that said carrier liquid can demonstrate a minimal water-miscibility to an extent that the capsule is formable.

In a preferred embodiment, the capsules according to the instant invention are prepared with at least one compound selected from compounds above-defined in (b), which is dissolved or dispersed in the carrier liquid.

In another preferred embodiment, the capsule according to the instant invention is prepared with a pesticide as defined in (a), which is dissolved or dispersed in the carrier liquid.

The below-mentioned pesticides are active ingredients for use in the agrochemical industry. A description of their structure as well as other pesticides (e.g., fungicides and insecticides) can be found in the e-Pesticide Manual, version 3.1, 13th Edition, Ed. CDC Tomlin, British Crop Protection Council, 2004-05. The number following the compound name is the entry number given in the Pesticide Manual.

In a preferred embodiment, the capsules according to the instant invention are characterized by the encapsulation of an insecticide, which is at least active via ingestion and is photolabile, selected from emamectin (291), spinosad (737), milbemectin (557), abamectin (1), profenofos (662), lufenuron (490), thiodicarb (799), lambda-cyhalothrin (198), fenoxycarb (340), deltamethrin (223), thiacloprid (791), triflumuron (835), silafluofen (728), tebufenozide (762), aldicarb (16), methoxyfenozide (535), chlorpyrifos methyl (146), indoxacarb (465), chlorfenapyr (130) and fipronil (354).

This pesticide is more preferably selected from emamectin, chlorfenapyr, spinosad, milbemectin, fipronil, profenofos, deltamethrin, lambda-cyhalothrin, indoxacarb and abamectin.

This pesticide is even more preferably emamectin, spinosad or fipronil. In an embodiment, an insecticide synergist, such as piperonyl butoxide (649), is used in combination with the pesticide. A combination of fipronil and piperonyl butoxide is particularly effective in the capsules according to the invention.

In a preferred embodiment, the capsules according to the instant invention are prepared with at least one other pesticide (co-pesticide), such as another insecticide which could be stomach active or not, a fungicide or an herbicide which would broaden the spectrum of pest control of pesticide (a). Therefore, pesticides (a) which are stomach active and photolabile as above-defined can be used as co-pesticides.

Examples of co-pesticides are acephate (2), acetamiprid (4), acetoprole (1-[5-amino-1-[2,6-dichloro-4-(trifluoromethyl)phenyl]-4-(methylsulfinyl)-1H-pyrazol-3-yl]ethanone), alpha-cypermethrin (202), azinphos-methyl (45), azoxystrobin (47), benalaxyl (56), benalaxyl-M (methyl N-(2,6-dimethylphenyl)-N-(phenylacetyl)-D-alaninate), benclothiaz (7-chloro-1,2-benzisothiazole), bendicoarb (58), benfuracarb (60), benomyl (62), bensultap (66), bifenthrin (76), bitertanol (84), boscalid, (88) captan (114), carbendazim (116), carbaryl (115), carbofuran (118), carbosulfan (119), carboxin (120), carbpropamid (2,2-dichloro-N-[1-(4-chlorophenyl)ethyl]-1-ethyl-3-methylcyclopropanecarboxamide), chlorothalonil (142), chlorpyrifos-methyl (146), clothianidin (165), copper salts (such as copper sulfate (172), cuprous oxide (181), Bordeaux mixture (87), copper hydroxide (169), copper sulfate (tribasic) (173), copper oxychloride (171) and copper octanoate (170)), cymoxanil (200), cypermethrin (201), cyproconazole (207), cyprodinil (208), cyromazine (209), dazomet (216), diazinon (227), difenoconazole (247), dimethoate (262), dimoxystrobin (266), diniconazole (267), dinotefuran (271), ethaboxam (N-(cyano-2-thienylmethyl)-4-ethyl-2-(ethylamino)-5-thiazolecarboxamide), ethirimol (5-butyl-2-(ethylamino)-6-methyl-4(1H-pyrimidinone), ethiprole (310), ethoprophos (312), famoxadone (322), fenamidone (325), fenamiphos (326), fenhexamid (334), fenpiclonil (341), flonicamid (358), fluoxastrobin (382), fluazinam (363), fludioxonil (368), fluquinconazole (385), flutolanil (396), flutriafol (397), fonophos (O-ethyl S-phenyl ethylphosphonodithioate), fosetyl-aluminium (407), fuberidazole (409), furathiocarb (412), gamma-cyhalothrin (197), gamma-HCH (430), guazatine (422), heptenophos (432), hexaconazole (435), hymexazol (447), imazalil (449), imidacloprid (458), ipconazole (468), iprodione (470), isofenphos (1236), mancozeb (496), maneb (497), metalaxyl (516), metalaxyl-M (517), metconazole (525), methiocarb (530), methyl-bromide (537), methyl-iodide (542), myclobutanil (564), nitempyram (579), nuarimol (587), omethoate (594), oxamyl (602), oxadixyl (601), oxine-copper (605), oxolinic acid (606), pencycuron (620), pefurazoate (618), phosmet (638), picoxystrobin (647), pirimicarb (651), prochloraz (659), procymidone (660), propamocarb (668), propiconazole (675), prothioconazole (685), pymetrozine (688), pyraclostrobin (690), pyrimethanil (705), pyroquilon (710), quintozene (716), silthiofam (729), tebuconazole (761), tefluthrin (769), terbufos (773), tetraconazole (778), thiabendazole (790), thiamethoxam (792), thiophanate-methyl (802), thiram (804), tolylfluanid (1,1-dichloro-N-[(dimethylamino)sulfonyl]-1-fluoro-N-(4-methylphenyl)methanesulfenamide), triadimenol (815), triazamate (818), triazophos (820), triazoxide (821), triticonazole (842), trifloxystrobin (832), 3-Iodo-N*2*-(2-methanesulfonyl-1,1-dimethyl-ethyl)-N*1*-[2-methyl-4-(1,2,2,2-tetrafluoro-1-trifluoromethyl-ethyl)-phenyl]-phthalamide (code NNI-0001), and a compound of 2-Pyridin-2-yl-2H-pyrazole-3-carboxylic acid (2-methylcarbamoyl-phenyl)-amide (code DKI-0001), such as 2-(3-Chloro-pyridin-2-yl)-5-trifluoromethyl-2H-pyrazole-3-carboxylic acid (4-chloro-2-isopropylcarbamoyl-6-methyl-phenyl)-amide, 2-(3-Chloro-pyridin-2-yl)-5-trifluoromethyl-2H-pyrazole-3-carboxylic acid (4-chloro-2-methyl-6-methylcarbamoyl-phenyl)-amide, 5-Bromo-2-(3-chloro-pyridin-2-yl)-2H-pyrazole-3-carboxylic acid (4-chloro-2-isopropylcarbamoyl-6-methyl-phenyl)-amide, and 5-Bromo-2-(3-chloro-pyridin-2-yl)-2H-pyrazole-3-carboxylic acid (4-chloro-2-methyl-6-methylcarbamoyl-phenyl)-amide.

In a first embodiment, said co-pesticide is co-encapsulated within the capsules according to the instant invention as above described.

In other preferred embodiments, said co-pesticide is incorporated into the composition as a tank-mix prepared extemporaneously with commercially available co-pesticide compositions (formulations) or is prepared as a pre-mix with the encapsulated composition.

Other formulation auxiliaries may also be used so long as the auxiliaries do not adversely interfere with the base triggering of the capsule.

As with the nature of the formulations, the methods of application, such as foliar, drench, spraying, atomizing, dusting, scattering, coating or pouring, are chosen in accordance with the intended objectives and the prevailing circumstances.

The tank-mix compositions are generally prepared by diluting with a solvent (for example, water) the one or more pre-mix compositions containing different pesticides, and optionally further auxiliaries. In this context, one of said pre-mix is the composition containing the capsule in which a pesticide which is active via ingestion and is photolabile is encapsulated. The second pre-mix can be another composition containing a co-pesticide.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilizers.

The formulations are prepared in a known manner, e.g., by homogeneously mixing and/or grinding the active ingredients with extenders, e.g., solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g., for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable nonsorbent carriers are, for example, calcite or sand. In addition, a great number of pregranulated materials of inorganic or organic nature can be used, e.g., especially dolomite or pulverized plant residues.

Depending upon the nature of pesticide which is at least active via ingestion and is photolabile and of the co-pesticide to be formulated, suitable surface-active compounds are nonionic and/or cationic and/or anionic surfactants having good emulsifying, dispersing and wetting properties. The term "surfactants" will also be understood as comprising mixtures of surfactants.

Particularly advantageous application-promoting adjuvants are also natural or synthetic phospholipids of the cephalin and lecithin series, e.g., phosphatidylethanolamine, phosphatidylserine, phosphatidylglycerol and lysolecithin.

Whereas commercial products will preferably be formulated as concentrates (e.g., pre-mix composition (formulation)), the end user will normally employ dilute formulations (e.g., tank mix composition).

The photoprotection of the above-mentioned pesticide, which is preferably an insecticide, at least active via ingestion and photolabile, is provided by the co-encapsulation of at least one compound selected from the compounds above-listed in (b).

The photoprotection of the above-mentioned pesticide (a), which is preferably an insecticide, and more preferably emamectin benzoate, fipronil or spinosad, most preferably emamectin, is advantageously provided by the co-encapsulation of at least one preferred compound selected from the compounds listed in (b) above, preferably 1-[[2,5-dimethyl-4-[(2-methylphenyl)azo]phenyl]azo]-2-naphthalenol, 1-[[4-[(dimethylphenyl)azo]dimethylphenyl]azo]-2-naphthalenol, 1-(ortho-tolylazo)-2-naphthol, 1-[[4-(phenyl)azo)phenyl]azo]-2-naphthalenol, 1-[[3-methyl-4-[(3-methylphenol)azo]phenyl]azo]-2-naphthalenol, 2,3-dihydro-2,2-dimethyl-6-[[4-(phenylazo)-1-naphthalenyl]azo]-1H-perimidine, 1-(phenylazo)-2-naphthalenol, 1-[[2-methyl-4-[(2-methylphenol)azo]phenyl]azo]-2-naphthalenol, and each thereof optionally in combination with a butylated hydroxy anisole.

In one particular aspect of this invention, emamectin benzoate, fipronil or spinosad, preferably emamectin, and at least one photoprotectant selected from the compounds above-listed in (b), are encapsulated within an aminoplast capsule containing one or more ester or thioester groups which are cleavable under basic conditions. The formation of this capsule wall occurs typically at a pH between 1 and 3 and at a temperature in the range from about 20° C. to about 100° C., preferably between about 40° C. and about 60° C. The aqueous solubility of emamectin benzoate increases appreciably at least below about pH 3, and it is surprising that only very minimal quantities of the pesticide are solubilised in the aqueous phase during the encapsulation process.

In another particular aspect of the invention,
  emamectin benzoate, fipronil or spinosad, preferably emamectin, and
  at least one photoprotectant selected from 1-[[2,5-dimethyl-4-[(2-methylphenol)azo]phenyl]azo]-2-naphthalenol, 1-[[4-[(dimethylphenyl)azo]dimethylphenyl]azo]-2-naphthalenol, 1-(ortho-tolylazo)-2-naphthol, 1-[[4-(phenyl)azo)phenyl]azo]-2-naphthalenol, 1-[[3- methyl-4-[(3-methylphenol)azo]phenyl]azo]-2-naphthalenol, 2,3-dihydro-2,2-dimethyl-6-[[4-(phenylazo)-1-naphthalenyl]azo]-1H-perimidine, 1-(phenylazo)-2-naphthalenol, 1-[[2-methyl-4-[(2-methylphenol)azo]phenyl]azo]-2-naphthalenol and each thereof optionally in combination with a butylated hydroxy anisole, are encapsulated within an aminoplast capsule as above-described.

In another preferred aspect of the invention, emamectin benzoate, fipronil or spinosad, preferably emamectin, and 1-[[4-[(dimethylphenyl)azo]dimethylphenyl]azo]-2-naphthalenol), optionally with a butylated hydroxy anisole are encapsulated within an aminoplast capsule as above-described.

In another preferred aspect of the invention, emamectin benzoate, fipronil or spinosad, preferably emamectin, and 1-[[2,5-dimethyl-4-[(2-methylphenol)azo]phenyl]azo]-2-naphthalenol, optionally with a butylated hydroxy anisole are encapsulated within an aminoplast capsule as above-described.

While not wishing to be bound by theory, the photoprotection of pesticides in the present invention may be achieved by compounds that operate by different photoprotection mechanisms. These include, inter alia, photon capture, radical scavenging and quenching of excited states.

Within the scope of the present invention, any ratio of the photoprotectant to active ingredient may be used. However, particularly preferred ratios use a minimal amount of photoprotectant to active ingredient to achieve the desired persistence. Such ratios generally make the encapsulation process more convenient and easier to handle and are economically favourable. Clearly, the presence of the photoprotectant should not interfere with the formation of the base sensitive barrier or capsule wall.

It has been found that the present invention is more selective in the targeting of harmful pests, by protecting beneficial arthropods that do not ingest the capsules, and allows reduced worker exposure hazards. Beneficial arthropods are to be understood as arthropods, mainly insects, that are important in the biological control of agronomic pests, typically through predatory or parasitic activity.

Furthermore, the use of the defined compound as a photoprotectant ensures that the pesticide's efficacy is adequately prolonged, but at same time ensuring that the pesticide biodegrades.

The method according to the instant invention is used advantageously for controlling damage of a material by a pest having an alkaline gut environment.

A skilled person would identify from the following pests list, which pests are known for having an alkaline pH gut condition. However, it is clear that said alkaline pH gut condition depends as well on the development stage of the pest (for example larvae, etc. . . . ), but also on the type of nutriment ingested by the pest (for example different kind of crops or plants).

The term "pest" shall be understood to mean insects or representatives of the order Acarina.

The insects of the order Lepidoptera are for example, *Acleris* spp., *Adoxophyes* spp., *Aegeria* spp., *Agrotis* spp., *Alabama argillaceae*, *Amylois* spp., *Anticarsia gemmatalis*, *Archips* spp., *Argyrotaenia* spp., *Astylus atromaculatus*, *Autographa* spp., *Busseola fusca*, *Cadra cautella*, *Carposina nipponensis*, *Chilo* spp., *Choristoneura* spp., *Clysia ambiguella*, *Cnaphalocrocis* spp., *Cnephasia* spp., *Cochylis* spp., *Coleophora* spp., *Crocidolomia binotalis*, *Cryptophlebia leucotreta*, *Cydia* spp., *Diatraea* spp., *Diparopsis castanea*, *Earias* spp., *Elasmopalpus* spp., *Ephestia* spp., *Eucosma* spp., *Eupoecilia ambiguella*, *Euproctis* spp., *Euxoa* spp., *Grapholita* spp., *Hedya nubiferana*, *Heliothis* spp., *Hellula undalis*, *Heteronychus arator*, *Hyphantria cunea*, *Keiferia lycopersicella*, *Leucoptera scitella*, *Lithocollethis* spp., *Lobesia botrana*, *Lymantria* spp., *Lyonetia* spp., *Malacosoma* spp., *Mamestra brassicae*, *Manduca sexta*, *Operophtera* spp., *Ostrinia nubilalis*, *Pammene* spp., *Pandemis* spp., *Panolis flammea*, *Pectinophora gossypiella*, *Phthorimaea operculella*, *Pieris rapae*, *Pieris* spp., *Plutella xylostella*, *Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;

The insects of the order Coleoptera are for example, *Agriotes* spp., *Anthonomus* spp., *Atomaria linearis*, *Chaetocnema tibialis*, *Conotrachelus* spp., *Cosmopolites* spp., *Curculio* spp., *Dermestes* spp., *Diabrotica* spp., *Dilopoderus* spp., *Epilachna* spp., *Eremnus* spp., *Heteronychus* spp., *Leptinotarsa decemlineata*, *Lissorhoptrus* spp., *Melolontha* spp., *Melolontha melolontha*, *Orycaephilus* spp., *Otiorhynchus* spp., *Phlyctinus* spp., *Popillia* spp., *Popillia japonica*, *Psylliodes* spp., *Rhizopertha* spp., Scarabeidae, *Somaticus* spp., *Sitophilus* spp., *Sitotroga* spp., *Tanymecus* spp., *Tenebrio* spp., *Tribolium* spp., *Trogoderma* spp., *Phyllotreta* spp., *Ceutorhynchus* spp., *Cyclocephala hirta*, *Cyclocephala pasadenae*, *Macrodactylus subspinosus*, *Macrodactylus uniformis* and *Zabrus* spp.;

The insects of the order Orthoptera are for example, *Blatta* spp., *Blattella* spp., *Gryllotalpa* spp., *Leucophaea maderae*, *Locusta* spp., *Periplaneta* spp. and *Schistocerca* spp.;

The insects of the order Psocoptera are for example *Liposcelis* spp.;

The insects of the order Anoplura are for example, *Haematopinus* spp., *Linognathus* spp., *Pediculus* spp., *Pemphigus* spp. and *Phylloxera* spp.;

The insects of the order Isoptera are for example, *Reticulitermes* spp. such as *R. flavipes*, *R. hesperus*, *R. tibialis*, *R. virginicus*, *R. santonensis*, *R. hageni*, *Coptotermes* spp., such as *C. formosanus*, *Nasutitermes* ssp. and *Macrotermes* spp.;

The insect of the order Mallophaga are for example, *Damalinea* spp. and *Trichodectes* spp.;

The insects of the order Thysanoptera are for example, *Frankliniella* spp., *Hercinothrips* spp., *Taeniothrips* spp., *Thrips palmi*, *Thrips tabaci* and *Scirtothrips aurantii*;

The insects of the order Heteroptera are for example, *Cimex* spp., *Distantiella theobroma*, *Dysdercus* spp., *Euchistus* spp. *Eurygaster* spp. *Leptocorisa* spp., *Nezara* spp., *Piesma* spp., *Rhodnius* spp., *Sahlbergella singularis*, *Scotinophara* spp. and *Triatoma* spp.;

The insects of the order Homoptera are for example, *Aleurothrixus floccosus*, *Aleyrodes brassicae*, *Aonidiella* spp., *Aphididae*, *Aphis* spp., *Aspidiotus* spp., *Bemisia tabaci*, *Ceroplaster* spp., *Chrysomphalus aonidium*, *Chrysomphalus dictyospermi*, *Coccus hesperidum*, *Empoasca* spp., *Eriosoma larigerum*, *Erythroneura* spp., *Gascardia* spp., *Laodelphax* spp., *Lecanium corni*, *Lepidosaphes* spp., *Macrosiphus* spp., *Myzus* spp., *Nephotettix* spp., *Nilaparvata* spp., *Paratoria* spp., *Pemphigus* spp., *Planococcus* spp., *Pseudaulacaspis* spp., *Pseudococcus* spp., *Psylla* spp., *Pulvinaria aethiopica*, *Quadraspidiotus* spp., *Rhopalosiphum* spp., *Saissetia* spp., *Scaphoideus* spp., *Schizaphis* spp., *Sitobion* spp., *Trialeurodes vaporariorum*, *Trioza erytreae* and *Unaspis citri*;

The insects of the order Hymenoptera are for example, *Acromyrmex*, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Solenopsis* spp. and *Vespa* spp.;

The insects of the order Diptera are for example, *Aedes* spp., *Antherigona soccata*, *Bibio hortulanus*, *Calliphora erythrocephala*, *Ceratitis* spp., *Chrysomyia* spp., *Culex* spp., *Cuterebra* spp., *Dacus* spp., *Drosophila melanogaster*, *Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis pomonella*, *Sciara* spp., *Stomoxys* spp., *Tabanus* spp., *Tannia* spp., *Delia* spp., *Anopheles* spp. and *Tipula* spp.;

The insects of the order Siphonaptera are for example, *Ceratophyllus* spp. and *Xenopsylla cheopis*; or The insects of the order Thysanura are for example, *Lepisma saccharina*.

Amongst the representatives of the order Acarina, for example, *Acarus siro*, *Aceria sheldoni*, *Aculus schlechtendali*, *Amblyomma* spp., *Argas* spp., *Boophilus* spp., *Brevipaipus* spp., *Bryobia praetiosa*, *Calipitrimerus* spp., *Chorioptes* spp., *Dermanyssus gallinae*, *Eotetranychus carpini*, *Eriophyes* spp., *Hyalomma* spp., *Ixodes* spp., *Olygonychus pratensis*, *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Tarsonemus* spp. and *Tetranychus* spp.

In the instance pesticide (a) is used in combination with another pesticide, the composition of the present invention would be suitable for control of a wider spectrum of pests, such as fungi, weeds or nematodes.

In a preferred embodiment, the method according to the instant invention is used advantageously for controlling damage of a material by a pest having an alkaline gut environment. Said pest having an alkaline gut environment is preferably an insect.

In a further preferred embodiment, the insect is of the order Lepidoptera.

In another preferred embodiment, the insect of is the order Coleoptera.

In another preferred embodiment, the insect is of the order Diptera.

In another preferred embodiment, the insect is a of the order Isoptera.

The term material according to the instant invention refers for example to agronomic material, which shall be understood to mean plants, especially useful plants (i.e., plants having a value, e.g., a monetary value to the grower, such as crops) and ornamentals in agriculture, in horticulture and in forestry (e.g. forest, greenhouse, nursery or ornamental plants not grown in a field, turf (e.g. commercial, golf, residential, recreational)), or parts of such plants, such as fruits, blossoms, leaves, stems, tubers or roots.

Target crop plants include especially field crops fruits, vegetables, nuts, berries, tropical plantations, ornamentals and others, such as wheat, barley, rye, oats, rice, maize, sorghum, beans, lentils, peas, soybeans, rape, mustard, poppy, sugar- and fodder-beet, cotton, flax, hemp, jute, sunflowers, castor oil, groundnuts, potatoes, sweet potatoes, tobacco, sugar cane, apples, pears, plums, peaches, nectarines, apricots, cherries, oranges, lemons, grapefruit, mandarins, olives vines, hops, almonds, walnuts, hazelnuts, avocado, bananas, tea, coffee, coconut, cocoa, natural rubber plants, oil plants, grapes strawberries, raspberries, blackberries, spinach, lettuce, asparagus, cabbages, chinese kale, carrots, onions, tomatoes, cucumbers, pepper, eggplants, melons, paprika, chilli, roses, chrysanthemums, cotton and carnations.

The plants can also be genetically modified.

The rate and frequency of use of the pesticide on the plant may vary within wide limits and depends on the specific pesticide, type of use, the nature of the soil, the method of application (pre- or post-emergence, etc.), the plant or pest to be controlled, the prevailing climatic conditions, and other factors governed by the method of application, the time of application and the target plant.

Typical application rate of pesticide can range from 5 to 300 g per hectare (g/ha). Examples of application rates for emamectin, spinosad and fipronil are:

|  | typical | preferred | more peferred |
|---|---|---|---|
| emamectin | 5-100 g/ha | 5-50 g/ha | 7-15 g/ha |
| fipronil | 10-200 g/ha | 30-100 g/ha | 35-75 g/ha |
| spinosad | 10-250 g/ha | 20-200 g/ha | 40-160 g/ha |

Alternatively, the term material refers to "non agronomic material" which shall be understood to mean wood products, public (human) and animal health, domestic and commercial structure, construction material, household and store product applications.

The following Examples are given by way of illustration and not by way of limitation of the invention.

EXAMPLES 1A-1V

Screen for Substances that Photoprotect Emamectin Benzoate

The following examples show that screening emulsifiable concentrate (EC) formulations comprising both the insecticide and the photoprotectants can identify preferred photoprotectants for emamectin benzoate.

The photoprotectant to be screened was either dissolved or dispersed in a simple Solvesso 200 based EC formulation containing 2% w/w emamectin benzoate, 10% w/w Soprophor BSU and 3% w/w phenyl sulfonate calx. The weight ratio of photoprotectant to insecticide was 1:1.

The ECs were diluted in water to the typical field application rate of emamectin benzoate, 10 g ai/ha at a spray volume of 200 l/ha. 2 μl droplets were applied to clean glass microscope slides and allowed to dry prior to being irradiated in an Atlas XLS+ Suntest artificial sunlight simulator, which employs a filtered xenon light source providing a spectral energy distribution similar to natural outdoor exposure. After irradiation, deposits were removed from the glass slides by a solvent wash and quantified by high performance liquid chromatography (HPLC) with mass-spectrometric (MS) detection.

The screening results are collated in Table 1 where the numbers 1 or 3 rate the performance of the photostabiliser relative to the non-photostabilised EC. #1 represents no improvement whilst #3 represents those photoprotectants that conferred a significant improvement in photostability. Selected photoprotectants were subsequently co-encapsulated with emamectin benzoate as described in Examples 4 to 25.

TABLE 1

List of potential photoprotectants for emamectin benzoate

| Example No | Photoprotectant | Screen Result | Encapsulated in Example |
|---|---|---|---|
| 1A | monosodium 1-amino-9,10-dihydro-9,10-dioxo-4-(phenylamino)-2-anthracenesulfonate | 3 | |
| 1B | 1,4-bis[(1-methylethyl)amino]-9,10-anthracenedione | 3 | 6 |
| 1C | monosodium 4-[(2-hydroxy-1-naphthalenyl)azo]-3-methyl-benzenesulfonate | 3 | |
| 1D | 4-[(4-nitrophenyl)azo]-N-phenyl-benzenamine | 3 | |
| 1E | 4-[[4-(phenylazo)-1-naphthalenyl]azo]-phenol | 3 | |
| 1F | 3-[ethyl[4-[(4-nitrophenyl)azo]phenyl]amino]-propanenitrile | 3 | |
| 1G | 4-[(4-nitrophenyl)azo]-benzenamine | 3 | |
| 1H | 1-[[2,5-dimethyl-4-[(2-methylphenol)azo]phenyl]azo]-2-naphthalenol | 3 | 15, 22, 23, 24 |
| 1I | 1-[[4-[(dimethylphenyl)azo]dimethylphenyl]azo]-2-naphthalenol | 3 | 11, 14, 19, 20, 21, 25 |
| 1J | 1-(ortho-tolylazo)-2-naphthol | 3 | 12 |
| 1K | 1-[[4-(phenyl)azo]phenyl]azo]-2-naphthalenol | 3 | 16 |
| 1L | 1-[[3-methyl-4-[(3-methylphenol)azo]phenyl]azo]-2-naphthalenol | 3 | 17 |
| 1M | 2,3-dihydro-2,2-dimethyl-6-[[4-(phenylazo)-1-naphthalenyl]azo]-1H-perimidine | 3 | |
| 1N | 1-(phenylazo)-2-naphthalenol | 3 | 7 |
| 1O | 1-[[2-methyl-4-[(2-methylphenol)azo]phenyl]azo]-2-naphthalenol | 3 | 13, 18 |
| 1P | 1:1 mixture of 1-(phenylazo)-2-naphthalenol with 1,4-bis[(1-methylethyl)amino]-9,10-anthracenedione | 3 | 10 |
| 1Q | mixture of 1-(phenylazo)-2-naphthalenol with 1,4-bis[(1-methylethyl)amino]-9,10-anthracenedione and 1-[[2-methyl-4-[(2-methylphenol)azo]phenyl]azo]-2-naphthalenol | 3 | |
| 1R | propanedioic acid, [(4-methoxy-phenyl)-methylene]-, bis(1,2,2,6,6-pentamethyl-4-piperidinyl)ester | 3 | |
| 1S | 2,2'-thiobis[4-t-octylphenolato]-beta-butylamine nickel (II) | 3 | |
| 1T | zinc oxide | 1 | |
| 1U | titanium dioxide | 1 | |
| 1V | 1:1 mixture of zinc oxide + titanium dioxide | 1 | |

Examples 2 and 3 illustrate the encapsulation of emamectin benzoate in aminoplast capsules that contain base triggerable moieties.

Emamectin benzoate was encapsulated using the following process according to the recipes given in Table 2. Emamectin benzoate technical was dissolved in a mixture of Solvesso 200 and octylmethoxycinnamate, to which Cymel U80 (equivalent to Beetle 80) (partially butylated urea-formaldehyde resin supplied by Cytec Industries), pentaerythritol tetrakis(2-mercaptoacetate) (henceforth abbreviated to PTT) and PMGTM were added. This solution was emulsified into a solution of Gohsenol GL05, Gohsenol GM-14L (polyvinylalcohols supplied by Nippon Gohsei) and Petro BAF (alkyl naphthalane sulfonate supplied by Witco) in water. The resultant emulsion was reduced to pH2 by the addition of sulphuric acid, followed by paddle stirring for 3 hours at 55° C., and post-formulation with sodium hydroxide such that the final pH of the formulation was in the range pH5-7.

PMGTM is a base-sensitive crosslinker prepared as described in WO00/05951 example 1J.

TABLE 2

Capsule suspensions (CS) of emamectin benzoate

| | Example 2 | Example 3 |
|---|---|---|
| Emamectin benzoate technical | 1.03 g | 1.03 g |
| Solvesso 200 | 14.0 g | 14.0 g |
| Octylmethoxycinnamate | 2.0 g | 2.0 g |

TABLE 2-continued

Capsule suspensions (CS) of emamectin benzoate

| | Example 2 | Example 3 |
|---|---|---|
| Cymel U80 | 3.3 g | 3.3 g |
| PTT | — | 0.21 g |
| PMGTM | 0.41 g | 0.21 g |
| Gohsenol GL05 | 0.8 g | 0.8 g |
| Gohsenol GM-14L | 0.9 g | 0.9 g |
| Petro BAF | 0.5 g | 0.5 g |
| Water | to 50 g | to 50 g |

EXAMPLES 4-25

Coencapsulation of Emamectin Benzoate with Photoprotectants

Examples 4-25 illustrate the encapsulation of emamectin benzoate according to the process described in examples 2-3 with the additional step of dissolving one or more photoprotectants together with the emamectin benzoate at the start of the process. Capsule suspensions were prepared according to the recipes given in Table 3.

TABLE 3

Capsule Suspensions of emamectin benzoate and photoprotectants

|  | Example 4 | Example 5 | Example 6 | Example 7 | Example 8 | Example 9 |
|---|---|---|---|---|---|---|
| Emamectin benzoate technical | 1.03 g | 1.03 g | 1.03 g | 1.03 g | 1.03 g | 1.03 g |
| Photoprotectant # | Note 1 | Note 2 | Example 1B | Example 1N | Note 3 | Note 4 |
| Photoprotectant mass | 1.0 g | 1.0 g | 0.5 g | 1.0 g | 0.5 g | 0.25 g |
| Solvesso 200 | 14.0 g | 14.0 g | 14.0 g | 14.0 g | 14.0 g | 14.0 g |
| Octylmethoxycinnamate | 2.0 g | 2.0 g | 2.0 g | 2.0 g | 2.0 g | 2.0 g |
| Cymel U80 | 3.3 g | 3.3 g | 3.3 g | 3.3 g | 3.3 g | 3.3 g |
| PMGTM | 0.41 g | 0.41 g | 0.41 g | 0.41 g | 0.41 g | 0.41 g |
| Gohsenol GL05 | 0.8 g | 0.8 g | 0.8 g | 0.8 g | 0.8 g | 0.8 g |
| Gohsenol GM-14L | 0.9 g | 0.9 g | 0.9 g | 0.9 g | 0.9 g | 0.9 g |
| Petro BAF | 0.5 g | 0.5 g | 0.5 g | 0.5 g | 0.5 g | 0.5 g |
| Water | to 50 g | to 50 g | to 50 g | to 50 g | to 50 g | to 50 g |

|  | Example 10 | Example 11 | Example 12 | Example 13 |
|---|---|---|---|---|
| Emamectin benzoate technical | 1.03 g | 1.03 g | 1.03 g | 1.03 g |
| Photoprotectant # | Example 1P | Example 1I | Example 1J | Example 1O |
| Photoprotectant mass | 1.0 g | 1.0 g | 1.0 g | 1.0 g |
| Solvesso 200 | 12.97 g | 13.0 g | 13.0 g | 13.0 g |
| Octylmethoxycinnamate | 2.0 g | 2.0 g | 2.0 g | 2.0 g |
| Cymel U80 | 3.3 g | 3.3 g | 3.3 g | 3.3 g |
| PMGTM | 0.41 g | 0.41 g | 0.41 g | 0.41 g |
| Gohsenol GL05 | 0.8 g | 0.8 g | 0.8 g | 0.8 g |
| Gohsenol GM-14L | 0.9 g | 0.9 g | 0.9 g | 0.9 g |
| Petro BAF | 0.5 g | 0.5 g | 0.5 g | 0.5 g |
| Water | to 50 g | to 50 g | to 50 g | to 50 g |

|  | Example 14 | Example 15 | Example 16 | Example 17 | Example 18 |
|---|---|---|---|---|---|
| Emamectin benzoate technical | 1.03 g | 1.03 g | 1.03 g | 1.03 g | 1.03 g |
| Photoprotectant # | Example 1I | Example 1H | Example 1K | Example 1L | Example 1O |
| Photoprotectant mass | 0.25 g | 0.25 g | 0.25 g | 0.25 g | 0.25 g |
| Solvesso 200 | 14.72 g | 13.72 g | 13.72 g | 13.72 g | 13.72 g |
| Octylmethoxycinnamate | 2.0 g | 2.0 g | 2.0 g | 2.0 g | 2.0 g |
| Cymel U80 | 3.3 g | 3.3 g | 3.3 g | 3.3 g | 3.3 g |
| PTT | 0.21 g | 0.21 g | 0.21 g | 0.21 g | 0.21 g |
| PMGTM | 0.21 g | 0.21 g | 0.21 g | 0.21 g | 0.21 g |
| Gohsenol GL05 | 0.8 g | 0.8 g | 0.8 g | 0.8 g | 0.8 g |
| Gohsenol GM-14L | 0.9 g | 0.9 g | 0.9 g | 0.9 g | 0.9 g |
| Petro BAF | 0.5 g | 0.5 g | 0.5 g | 0.5 g | 0.5 g |
| Water | to 50 g | to 50 g | to 50 g | to 50 g | to 50 g |

|  | Example 19 | Example 20 | Example 21 | Example 22 | Example 23 | Example 24 | Example 25 |
|---|---|---|---|---|---|---|---|
| Emamectin benzoate technical | 1.03 g | 1.03 g | 1.03 g | 2.05 g | 2.05 g | 1.03 g | 1.03 g |
| Photoprotectant A | Example 1I | Example 1I | Example 1I | Example 1H | Example 1H | Example 1H | Example 1I |
| Photoprotectant A mass | 0.5 g | 0.5 g | 1.0 g | 2.0 g | 1.0 g | 0.5 g | 1.0 g |
| Photoprotectant B | — | Note 5 | — | — | Note 5 | — | — |
| Photoprotectant B mass | — | 0.5 g | — | — | 1.0 g | — | — |
| Solvesso 200 | 14.47 g | 14.47 g | 14.47 g | 25.95 g | 25.95 g | 13.47 g | 12.97 g |
| Octylmethoxycinnamate | 2.0 g | 2.0 g | 2.0 g | 4.0 g | 4.0 g | 2.0 g | 2.0 g |
| Cymel U80 | 3.3 g | 3.3 g | 3.3 g | 6.65 g | 6.65 g | 3.3 g | 3.3 g |
| PTT | 0.21 g | 0.21 g | 0.21 g | 0.41 g | 0.41 g | 0.21 g | 0.35 g |
| PMGTM | 0.21 g | 0.21 g | 0.21 g | 0.41 g | 0.41 g | 0.21 g | 0.07 g |
| Gohsenol GL05 | 0.8 g | 0.8 g | 0.8 g | 1.6 g | 1.6 g | 0.8 g | 0.8 g |
| Gohsenol GM-14L | 0.9 g | 0.9 g | 0.9 g | 1.8 g | 1.8 g | 0.9 g | 0.9 g |
| Petro BAF | 0.5 g | 0.5 g | 0.5 g | 1.0 g | 1.0 g | 0.5 g | 0.5 g |
| Water | to 50 g | to 50 g | to 50 g | to 100 g | to 100 g | to 100 g | to 100 g |

Note 1: Photoprotectant is tris(2,4-di-tert-butylphenyl)phosphite
Note 2: Photoprotectant is 2-hydroxy-4-n-octyloxybenzophenone
Note 3: Photoprotectant is 1,4-bis[(4-methylphenyl)amino]-9,10-anthacenedione
Note 4: Photoprotectant is 1-hydroxy-4-[(4-methylphenyl)amino]-9,10-anthacenedione.
Note 5: Photoprotectant is butylated hydroxy anisole (a mixture of 2 + 3-tert-butyl-4-methoxyphenols).

EXAMPLE 26

Photostability of Emamectin Benzoate Coencapsulated with Photoprotectants

The following example shows that a screening process can select preferred coencapsulated photoprotectants for emamectin benzoate.

The encapsulated formulations from examples 3, 6-11, 19-24 were diluted in water to the typical field application rate of emamectin benzoate, log active ingredient/ha at a spray volume of 200 l/ha. 2 µl droplets were applied to clean glass microscope slides and allowed to dry prior to being irradiated in an Atlas XLS+ Suntest artificial sunlight simulator that employs a filtered xenon light source providing a spectral energy distribution similar to natural outdoor exposure. After irradiation, deposits were removed from the glass slides and emamectin benzoate extracted from the capsules using a suitable solvent. Residues were subsequently quantified by high performance liquid chromatography (HPLC) with mass-spectrometric (MS) detection. Results are shown in FIGS. 1 and 2.

EXAMPLE 27

Contact Activity Test of the Triggered Release Capsules Against Spodoptera littoralis This example shows that the triggered release capsules show much lower contact activity against *Spodoptera littoralis* when applied at similar rates to a commercial standard (Proclaim) of emamectin benzoate that is not encapsulated. In combination with example 32, the data demonstrate that the triggered release capsules safen the formulation to beneficial insects.

Contact or topical activity was assessed by applying 1 µl of the test formulation described below at rates of 333, 100, 33 and 10 ppm by micropipette to an area just below the head capsule of L4 *S littoralis* larvae. Mortality was assessed after 96 hours. Results for the application rate of 33 ppm are given in Table 4.

In table 4, "SG" means "water-soluble granules", "CS" means "capsule suspension" and "AI" means "active ingredient".

TABLE 4

| Example | Test formulation | Formulation type | % mortality at 33 ppm AI |
|---|---|---|---|
| | Proclaim | SG | 80 |
| 27A | Example 3 | CS without photostabiliser | 5 |
| 27B | Example 21 | CS with photostabiliser | 0 |

EXAMPLE 28

Feeding Contact Activity of the Triggered Release Capsules Against Spodoptera littoralis This example shows that the triggered release capsules show a slightly reduced feeding contact activity against *Spodoptera littoralis* when applied at similar rates to a commercial standard (Proclaim) of emamectin benzoate that is not encapsulated. The data show that while the capsules show low activity by contact (examples 27 and 32) they are highly active towards crop consuming pests that have alkaline guts.

Feeding contact activity was assessed by feeding L2 *S littoralis* larvae on cotton leaves that had been previously sprayed with the test formulations described in Example 27 at 2, 1, 0.5, 0.25, and 0.125 ppm. Mortality was assessed after four days. Results for the application rate of 2 ppm are given in Table 5.

In table 5, "SG" means "water-soluble granules", "CS" means "capsule suspension" and "AI" means "active ingredient".

TABLE 5

| Example | Test formulation | Formulation type | % mortality at 2 ppm AI |
|---|---|---|---|
| | Proclaim | SG | 100 |
| 28A | Example 3 | CS without photostabiliser | 90 |
| 28B | Example 21 | CS with photostabiliser | 96 |

EXAMPLE 29

Control 10 Days After Application of Capsule Containing Emamectin Benzoate and a Photoprotectant on Spodoptera littoralis This example demonstrates that co-encapsulating the insecticide with a photoprotectant can extend the time over which emamectin benzoate is effective against *Spodoptera littoralis*.

Test formulations in Table 6 were applied at rates of 2.5, 5.0 and 10.0 grams of emamectin benzoate per hectare to *Gossypium barbadense* using a six-nozzle boom pressurised with $CO_2$ at a spray volume of 300 L/ha. Plants were exposed to direct sunlight. Sprayed fully developed green leaves were collected at 0, 1, 3, 7, 10, 13, 15, 18 and 20 days after application. The leaves were transferred to glass jars to each of which was added 20 L2 *Spodoptera littoralis* larvae. Larval mortality and leaf damage were assessed after 96 hours. The percentage control after 10 days for an application rate of 5 g/ha is given in Table 6. The commercial formulation Proclaim lost all pest control by day 13.

In table 6, "SG" means "water-soluble granules", "CS" means "capsule suspension" and "AI" means "active ingredient".

TABLE 6

| Example | Test formulation | Formulation type | % Control after 10 days (application rate 5 g ai/ha) |
|---|---|---|---|
| — | Untreated | | 0 |
| — | Proclaim | SG | 34 |
| 29A | Example 3 | CS without photostabiliser | 1 |
| 29B | Example 21 | CS with photostabiliser | 76 |

EXAMPLE 30

Screen for Selection of Preferred Ratios of Active Ingredient: Photoprotectant This example shows that the ratio of co-encapsulated photoprotectant to emamectin benzoate affects control of *Spodoptera littoralis* as a function of the time that the capsules are exposed to sunlight.

Test formulations were applied to cotton plants exposed to direct sunlight at rates of 5.0 and 10.0 grams of emamectin benzoate per hectare as described in Example 29.

Sprayed fully developed green leaves were collected at 0, 1, 3, 7, 10, and 13 days after application. The leaves were transferred to glass jars to each of which was added 12 *Spodoptera littoralis* larvae. Larval mortality was assessed after 96 hours. The percentage control after 10 days for the application of 10 g/ha of emamectin benzoate is shown in Table 7.

In table 7, "CS" means "capsule suspension".

TABLE 7

| Example | Test formulation | Formulation type | % Control after 10 days (application rate 10 g ai/ha) |
|---|---|---|---|
| | Proclaim | SG | 73 |
| 30A | Example 21 | CS with 2% w/w emamectin benzoate and 2% w/w photoprotectant example 1I* | 93 |
| 30B | Example 14 | CS with 2% w/w emamectin benzoate and 0.5% w/w photoprotectant example 1I* | 64 |

*Photoprotectant 1I: 1-[[4-[(dimethylphenyl)azo]dimethylphenyl]azo]-2-naphthalenol

EXAMPLE 31

Coencapsulation of Several Photoprotectants

This example shows that a co-encapsulated mixture of photoprotectants can extend the control of *Spodoptera littoralis* by emamectin benzoate.

The procedure described in Example 30 was used for the test formulations below. The percentage control after 10 days for the application of 10 g/ha of emamectin benzoate is shown in Table 8.

In table 8, "SG" means "water-soluble granules" and "CS" means "capsule suspension".

TABLE 8

| Example | Test formulation | Formulation type | % Control after 10 days (application rate 10 g ai/ha) |
|---|---|---|---|
| | Proclaim | SG | 73 |
| 31 | Example 20 | CS with 2% w/w emamectin benzoate and 1% w/w photoprotectant example 1I* and 1% photoprotectant Butylated Hydroxy Anisole* | 97 |

*Photoprotectant 1I: 1-[[4-[(dimethylphenyl)azo]dimethylphenyl]azo]-2-naphthalenol
*Photoprotectant Butylated Hydroxy Anisole: Mixture of 2 + 3-tert-butyl-4-methoxyphenols

EXAMPLE 32

Effect of Triggered Release Capsules of Emamectin Benzoate on Beneficial Arthropods This example shows that triggered release capsules of emamectin benzoate are safer to beneficial arthropods than is a non-encapsulated EC under the same conditions of either direct spraying or of exposure to residues.

EXAMPLE 32A

Activity Against *Typhlodromus pyri*

Overspray activity was assessed by directly spraying protonymphs of *Typhlodromus pyri* with the test formulation. Residual activity was assessed by exposing protonymphs of *T. pyri* to bean leaves that had been sprayed with the test formulations.

In table 9, "EC" means "emulsifiable concentrate" and "CS" means "capsule suspension".

TABLE 9

| Example | Test formulation | Formulation type |
|---|---|---|
| 32A | Proclaim | 1.92% w/v emamectin benzoate EC |
| | Example 21 | CS with 2% w/w emamectin benzoate and 2% w/w photoprotectant example 1I* |

*Photoprotectant 1I: 1-[[4-[(dimethylphenyl)azo]dimethylphenyl]azo]-2-naphthalenol The test procedure followed IOBC guidelines (Blümel et al., 2000, pp 121-143) and in both assessments emamectin benzoate was sprayed at a rate of 10 grams of ai per hectare and an application volume of 200 liters per hectare. Mortality (dead and escapees) was assessed at 3 and 7 days after treatment (DAT). Results for corrected mortality at 7 DAT are shown in Table 10.

TABLE 10

| Test formulation | Corrected mortality (%) 7 DAT | | |
|---|---|---|---|
| | Overspray | Residual | Combined |
| Control | — | — | |
| Example 21 | 15.8 | 10.0 | 11.0 |
| Proclaim | 100.0 | 100.0 | 100.0 |

EXAMPLE 32B

Contact and Oral Activity Against Honeybees (*Apis mellifera*)

The contact activity against honeybees (*Apis mellifera*) of the formulation described in Example 21 was assessed by respectively applying a 1 µL drop of test formulation in water to the back of a bee using a precision applicator. The dose applied was 0.05 µg active ingredient/bee. Mortality was assessed after 24 hours. Another test was undertaken where bees were fed a 50% sucrose solution containing the test formulation. The target dose was 0.07 ug active ingredient/bee. Mortality was assessed after 24 hours. Results are shown in Table 11.

In table 11, "EC" means "emulsifiable concentrate".

TABLE 11

| Test formulation | Mortality (%) 24 HAA | |
|---|---|---|
| | Contact | Oral |
| Emamectin benzoate EC | 100 | 40 |
| Example 21 | 0 | 0 |

The contact and oral activity of the triggered release formulation detailed in Example 21 is at least one order of magnitude lower than for an EC formulation containing emamectin benzoate.

EXAMPLE 33

Cytotoxicity Assay

This example demonstrates that the triggered release capsules of emamectin benzoate are less toxic to cultured cells than is a non-encapsulated emulsifiable concentrate (EC). The capsule suspension (CS) is thus predicted to cause less eye irritancy than the (EC).

The formulation detailed in Example 21 was assessed by the in vitro K562 Cytotoxicity Assay, which was used as part of the stepwise approach detailed by Lewis et al (1994), in Toxicology in Vitro, vol 8, pgs 865-866. This technique has been developed to predict materials of severe ocular irritancy in vivo against percent viability. A threshold value has been established as 85% below which, materials are considered likely to cause severe ocular irritation when tested in vivo. Results are shown in Table 12.

TABLE 12

|  | Test formulation | |
| --- | --- | --- |
|  | Example 21 | Proclaim |
| Group Size Of Four Readings | Percent Viability | Percent Viability |
| Control | 96.3 | 97.2 |
| Sample After Incubation | 90.2 | 0.0 |
| Percentage Of Control | 93.7 | 0.0 |

Proclaim 019EC caused a significant reduction in cell viability when compared to the control values following a 15-minute exposure and is therefore considered likely to cause severe ocular irritation in vivo. By contrast, under the same experimental conditions the emamectin benzoate CS formulation did not cause a significant reduction in cell viability and is therefore considered unlikely to cause severe ocular irritation in vivo.

The invention claimed is:

1. A method for controlling damage of a material by a pest, which comprises applying to the material a composition comprising a capsule which comprises:
   (a) emamectin and
   (b) 1-[[-3-methyl-4-[(3-methylphenol)azo]phenyl]azo]-2-naphthalenol;
      and each thereof optionally in combination with a butylated hydroxy anisole; and
   wherein said capsule comprises polymeric barrier or moieties and wherein the polymeric barrier or moieties within the polymeric barrier of the capsule are base cleavable.

2. The method according to claim 1 wherein the capsule is either a reservoir capsule or a matrix capsule.

3. The method according to claim 2 wherein the reservoir capsule contains a carrier liquid which is substantially water-immiscible.

4. The method according to claim 1 wherein at least one compound (b) is dissolved or dispersed in the carrier liquid.

5. The method according to claim 1 wherein the emamectin is dissolved or dispersed in the carrier liquid.

6. The method according to claim 1 wherein the capsule is dispersed in the composition in an aqueous medium.

7. The method according to claim 1 wherein the material is an agronomic material.

8. The method according to claim 1 wherein the material is a non-agronomic material.

9. The method according to claim 1 wherein the pest has an alkaline gut environment.

10. The method according to claim 9 wherein the pest is an insect having an alkaline gut environment.

11. The method according to claim 1 wherein the pest insect is of the order Lepidoptera, Coleoptera or Diptera.

12. The method according to claim 1 wherein the pest insect is of the order Isoptera.

13. A composition as defined in claim 1.

14. The composition according to claim 13 wherein the composition further comprises at least one additional pesticide.

15. A capsule as defined in claim 1.

16. The capsule according to claim 15 wherein the capsule further comprises at least one other pesticide.

17. The method according to claim 1, wherein (a) and (b) are co-encapsulated.

* * * * *